United States Patent [19]

Yoshida et al.

[11] Patent Number: 5,118,817

[45] Date of Patent: Jun. 2, 1992

[54] PROCESS FOR PRODUCTION OF 2-PHOSPHATED ESTERS OF ASCORBIC ACID

[75] Inventors: Kokichi Yoshida, Suita; Yasushi Kawashima, Amagasaki, both of Japan

[73] Assignee: Takeda Chemical Industries, Ltd., Osaka, Japan

[21] Appl. No.: 599,079

[22] Filed: Oct. 17, 1990

[30] Foreign Application Priority Data

Oct. 31, 1989 [JP] Japan .................................. 1-285800

[51] Int. Cl.$^5$ .............................................. C07F 9/09
[52] U.S. Cl. ........................................... 549/222
[58] Field of Search ..................................... 549/222

[56] References Cited

U.S. PATENT DOCUMENTS

| | | | |
|---|---|---|---|
| 3,671,549 | 6/1972 | Hinkley | 549/222 |
| 3,718,482 | 2/1973 | Hinkley | 549/222 |
| 3,749,680 | 7/1973 | Hinkley | 549/222 |
| 4,179,445 | 12/1979 | Sieb et al. | 549/222 |
| 4,647,672 | 3/1987 | Seib et al. | 549/222 |
| 4,939,128 | 7/1990 | Kato et al. | 549/222 |

FOREIGN PATENT DOCUMENTS

0339486  11/1989  European Pat. Off. .

OTHER PUBLICATIONS

Chem. Pharm. Bull. 17, No. 2, 1969, pp. 381-386, Nomura et al., "Studies on L-Ascorbic Derivatives. II. L-Ascorbic Acid 3-Phosphate and 3-Pyrophosphate." Carbohydrate Research, 67, pp. 127-138, 1973, Lee et al., "Chemical Synthesis of Several Phosphoric Esters of L-Ascorbic Acid."

*Primary Examiner*—C. Warren Ivy
*Assistant Examiner*—Amelia A. Owens
*Attorney, Agent, or Firm*—Wegner, Cantor, Mueller & Player

[57] ABSTRACT

A process for the production of 2-phosphated esters of ascorbic acid by subjecting an ascorbic acid optionally protected at the 5- and 6-positions to phosphorylation with maintaining the concentration of the optionally protected ascorbic acid in a reaction mixture at less than 0.3 M and, if necessary, removing any protecting group is disclosed. 2-Phosphated ester of ascorbic acid can be produced with a good yield in an industrial scale by this process.

11 Claims, No Drawings

PROCESS FOR PRODUCTION OF 2-PHOSPHATED ESTERS OF ASCORBIC ACID

FIELD OF THE INVENTION

The present invention relates to a process for the production of 2-phosphated esters of ascorbic acid.

BACKGROUND OF THE INVENTION

In medicinal preparations, food products and cosmetics containing ascorbic acid (vitamin C), it has been considered to be relatively difficult to maintain their commercial value over a long period of time because ascorbic acid has problems in its stability. An example of compounds being capable of solving such problems and, further, having excellent vitamin C activity is 2-phosphated esters of ascorbic acid. These compounds have already been known to convert into ascorbic acid in a living body, and the expansion of the use thereof for various purposes is expected.

2-Phosphated esters of ascorbic acid can be produced by phosphorylation of ascorbic acid. Although direct phosphorylation of ascorbic acid has been known (Japanese Patent Publication No. 43-9218, U.S. Pat. No. 3,671,549, Japanese Patent Publication No. 52-18191, etc.), those methods are far from being satisfactory as industrially applicable processes because a mixture of phosphoric acid compounds is produced, a yield is unsatisfactory and, further, the reaction is conducted in a nonaqueous system.

Therefore, in general, a 2-phosphated ester of ascorbic acid is produced by firstly protecting ascorbic acid with acetone to obtain 5,6-O-isopropylidene-L-ascorbic acid and then subjecting this protected compound to phosphorylation.

Regarding phosphorylation of 5,6-O-isopropylidene-L-ascorbic acid, various patents and literatures have been published [Japanese Patent Publication Nos. 43-9219, 45-4497, 45-30328 and 48-72163, U.S. Pat. No. 4,179,445, Carbohydrate Research, 67(1978) 127–138, etc.]. However, none of them provides any satisfactory yield.

Presumably, such unsatisfactory yields would mainly result from the fact that, in addition to inadequate reaction conditions, any method for accurately analyzing the objective compound in a reaction mixture has not yet been developed.

For example, in U.S. Pat. No. 4,179,445, the yields of 2-phosphated ester of ascorbic acid after phosphorylation appear to be high. However, when the yields are determined quantitatively by a method developed by the present inventors, they are at highest about 76% even under conditions disclosed therein for providing the highest yield.

OBJECTS OF THE INVENTION

The main object of the present invention is to provide an industrial method for the production of 2-phosphated esters of ascorbic acid in a good yield.

This object as well as other objects and advantages of the present invention will become apparent to those skilled in the art from the following description.

SUMMARY OF THE INVENTION

For investigating phosphorylation of ascorbic acid and the like, accurate analysis of 2-phosphated ester of ascorbic acid in a reaction mixture is indispensable for finding out optimal reaction conditions.

Then, the present inventors have intensively studied analytical methods by means of high performance liquid chromatography (HPLC), and have reached a conclusion that the following analytical method is most suitable.

Method of analyzing 2-phosphated esters of ascorbic acid by means of HPLC:

Column: Nucleosil $5NH_2$ 5 $\mu$m 4 mm$\phi \times$ 150 mm (manufactured by Gaschro Kogyo, Ltd., Japan)

Mobile Phase: Acetonitrile/0.1M $KH_2PO_4$ aqueous solution = $\frac{1}{2}$ (adjusting to pH 4.3 with phosphoric acid)

Flow Rate: 1 ml/min.

Temperature: 25° C.

Detection: UV 254 nm

Quantitative Determination: Comparison of a peak area with that of an authentic sample The present inventors have further studied various reaction conditions using this method intensively. As a result, it has been found that, when the reaction is conducted with maintaining unreacted ascorbic acid in a relatively low concentration during the reaction, a 2-phosphated ester of ascorbic acid can be produced in a yield of not less than 90%. Thus, the present invention has been completed.

Namely, according to the present invention, there is provided a process for the production of 2-phosphated esters of ascorbic acid which comprises subjecting an ascorbic acid optionally protected at the 5- and 6-positions to phosphorylation with maintaining the concentration of ascorbic acid in a reaction mixture at less than 0.3M and, if necessary, removing any protecting group.

DETAILED DESCRIPTION OF THE INVENTION

Examples of ascorbic acid protected at the 5- and 6-positions include ascorbic acid whose 5- and 6-positions are ketalized with an aliphatic ketone such as acetone, methyl ethyl ketone, cyclopentanone, cyclohexanone or the like. Specific examples thereof include 5,6-O-isopropylidene ascorbic acid, 5,6-O-sec-butylidene ascorbic acid, 5,6-O-1-ethylbutylidene ascorbic acid, 5,6-O-cyclopentylidene ascorbic acid or 5,6-O-cyclohexylidene ascorbic acid.

Particularly, ascorbic acid and 5,6-O-isopropylidene ascorbic acid are preferred as the starting compound of the process of the present invention.

The process of the present invention is generally conducted by dissolving the optionally protected ascorbic acid in water, preferably, in the presence of an organic base such as pyridine, adding dropwise a phosphorylating agent to the solution while controlling the pH with an aqueous solution of alkali, distilling off the organic base and then, if necessary, adjusting the pH to not higher than 1 to remove any protecting group.

In order to obtain a good yield, it is of importance to maintain the concentration of unreacted optionally protected ascorbic acid in a reaction mixture as low as about 0.3M or lower, preferably, 0.25M or lower. In the case of conducting the process of the present invention by adding dropwise the optionally protected ascorbic acid and a phosphorylating agent simultaneously, the concentration of unreacted optionally protected ascorbic acid in a reaction mixture can be maintained at a very low level. e.g., nearly about 0. When the concentration of the starting compound is higher than this level, the formation of by-products such as dimerized bis ascorbyl-2,2'-phosphate and the like increases, resulting in lowering of the yield.

The process of the present invention can be conducted by a continuous or batchwise operation. For example, a predetermined amount of the optionally protected ascorbic acid is placed in a reaction vessel, followed by adding dropwise a phosphorylating agent to the reaction vessel. After completion of the reaction, this operation can be repeated by using the same reaction vessel. However, from the industrial viewpoint, it is more advantageous to intermittently or continuously add dropwise a solution or crystals of the optionally protected ascorbic acid and a phosphorylating agent to a reaction system from outside during the reaction because of increase in the concentration of an objective product.

The phosphorylating agent is not specifically limited and any phosphorylating agent can be used for the reaction of the present invention. Examples of commonly used phosphorylating agents include phosphorus oxychloride, dichlorophosphoric acid, tetrachloropyrophosphoric acid as well as partial hydrate and partial alcoholate of phosphorus oxychloride.

The amount of a phosphorylating agent to be used is in the range of from about 1.5 to about 2.5 times the equivalent, preferably, from about 1.7 to about 2.2 times the equivalent of the optionally protected ascorbic acid used for the reaction. When the amount is not more than 1.5 times the equivalent, the yield tends to lower due to the remaining of unreacted starting compounds and by-production of the dimer and the like. On the other hand, when the amount of the phosphorylating agent is more than 2.5 times the equivalent, decomposition of the end product is caused, resulting in lowering of the yield. The time required for the addition of the phosphorylating agent is not limited. However, it is efficient to add dropwise the phosphorylating agent within 6 hours. However, when the phosphorylating agent is added within a too short period of time, it is difficult to control the temperature and pH.

The reaction is preferably conducted in the presence of an organic base such as pyridine. When the reaction is conducted in the absence of an organic base, undesirable by-products, i.e. the dimer and 3-phosphated esters of ascorbic acid, are formed in a large amount. The amount of the organic base is preferably in the range of from about 0.5 to about 5 times the molar quantity, particularly in the range of from about 1.5 to about 3.5 times the molar quantity of the optionally protected ascorbic acid used.

The reaction is preferably conducted with controlling the pH at about 12.5 to about 13.5. As a base for controlling the pH, an alkali metal hydroxide such as sodium hydroxide, potassium hydroxide or lithium hydroxide, or aqueous ammonia can be used.

The temperature is preferably maintained in the range of from about $-5°$ C. to about $10°$ C. during the reaction.

For reducing coloring of the reaction mixture, it is preferable to conduct the reaction of the present invention in an atmosphere of an inert gas, although this is not essential. Examples of the inert gas include nitrogen, argon and the like.

After completion of the reaction, if the organic base is used, it is distilled off from the reaction mixture containing the 2-phosphated ester of ascorbic acid thus produced. When the protected ascorbic acid is used, the desired 2-phosphated ester of ascorbic acid can be readily obtained by adding dropwise an acid to the reaction mixture to adjust the pH thereof to 1 or lower to remove the protecting group. This deprotection proceeds quantitatively. For adjusting the pH, mineral acids such as hydrochloric acid, sulfuric acid, nitric acid and the like can be used. Further, the deprotection can be conducted by passing the reaction mixture through a column packed with a H-type strong acidic ion-exchange resin.

If desired, a salt of 2-phosphated ester of ascorbic acid with an inorganic base such as sodium, potassium, magnesium or the like can be isolated in a highly pure state from the reaction mixture thus obtained by a conventional method.

As described hereinabove, according to the present invention, 2-phosphated ester of ascorbic acid can be produced with a good yield in an industrial scale.

The following examples, comparative examples and reference example further illustrate the present invention in detail, but are not to be construed to limit the scope thereof.

EXAMPLE 1

The following reaction was conducted under a nitrogen atmosphere.

Ascorbic acid (hereinafter abbreviated as VC) (8.2 g) was dissolved in a mixture of pyridine (7.4 ml) and water (193 ml) and the resulting solution was cooled to 0 to 5° C. A 60 w/v% aqueous solution of potassium hydroxide (about 9 ml) was added to the solution to adjust pH thereof to 12.7. To the resulting solution was added dropwise phosphorus oxychloride (14.2 g) over 1.5 hours with maintaining the temperature of the reaction system at 0 to 10° C. and maintaining the pH of the reaction system at 12.7±0.1 by the addition of a 60 w/v% aqueous solution of potassium hydroxide using a constant delivery pump (manufactured by Iwaki, Ltd., Japan, MM-2DS type) and a pH controller (Hirama Rikagaku Kenkyusho, Ltd., Japan, pH-CON-2 type). Then, the reaction mixture was stirred at the same temperature for about 30 minutes.

Pyridine was then distilled off under reduced pressure at a temperature not higher than 40° C. To the residue was added a 35% aqueous solution of hydrochloric acid to adjust the pH to 0.5. An analysis was conducted under the above-described HPLC conditions to determine the amount and the yield of the 2-phosphated ester of ascorbic acid in this solution. As an authentic sample, magnesium salt of 2-phosphated ester of ascorbic acid having a known purity was used.

As a result, the amount of the 2-phosphated ester of ascorbic acid thus produced and the yield percentage based on the amount of VC used were 9.6 g and 80.5%, respectively.

EXAMPLE 2

The following reaction was conducted under a nitrogen atmosphere.

VC (8.2 g) was dissolved in a mixture of pyridine (15 ml) and water (185 ml) and the solution was cooled to 0° to 5° C. The solution was adjusted to pH 12.7 by addition of a 60 w/v% aqueous solution of potassium hydroxide (about 9 ml). To the resulting solution was added dropwise phosphorus oxychloride (14.2 g) over about 1.5 hours with maintaining the temperature of the reaction system at 0° to 10° C. and maintaining the pH of the reaction system at 12.7±0.1 by the addition of a 60 w/v% aqueous solution of potassium hydroxide using the same devices as those used in Example 1. Then, the resulting mixture was stirred at the same temperature for about 30 minutes.

To the reaction mixture was added VC (8.2 g) over about 15 minutes with maintaining pH at 12.7±0.1. Then, phosphorus oxychloride (14.2 g) was again added dropwise thereto over about 1.5 hours with maintaining the temperature of the reaction system at 0° to 10° C. and maintaining the pH of the reaction system at 12.7±0.1 by the addition of a 60 w/v% aqueous solution of potassium hydroxide. Then, the mixture was stirred at the same temperature for additional 30 minutes. Pyridine was then distilled-off under reduced pressure at 40° C. or below. To the residue was then added a 35% aqueous solution of hydrochloric acid to adjust the pH to 0.5. The amount and the yield percentage of 2-phosphated ester of ascorbic acid were determined according to the same manner as that described in Example 1.

As a result, the amount of 2-phosphated ester of ascorbic acid and the yield percentage based on VC used were 19.7 g and 82.6%, respectively.

EXAMPLE 3

The following reaction was conducted under a nitrogen atmosphere.

VC (38.5 g) was dissolved in a mixture of pyridine (10 ml) and water (90 ml). A 20 ml portion of this solution was added dropwise over about 15 minutes to a mixture of pyridine (40 ml) and water (460 ml) cooled to 0° to 5° C. by using a constant delivery pump (manufactured by Iwaki, Ltd., Japan, MM-2DS type) with maintaining pH at 12.8±0.1 by addition of a 60 w/v% aqueous solution of potassium hydroxide with a constant delivery pump (Taiyo Kagaku Kogyo, Ltd., Japan, Decarf type) and a pH controller (Hirama Rikagaku Kenkyusho Ltd., Japan, pH-CON-2 type), and with cooling at 0° to 10° C.

Then, phosphorus oxychloride (67.4 g) and the remaining VC solution were added dropwise simultaneously with cooling at 0° to 10° C. by using respective constant delivery pumps (manufactured by Iwaki, Ltd., Japan, MM-2DS type) at constant flow rates so that the addition of phosphorus oxychloride was completed in 3 hours and that of the VC solution was completed in 2.5 hours, with maintaining the pH of the system at 12.8±0.1 by the addition of a 60 w/v% aqueous solution of potassium hydroxide with a constant delivery pump (manufactured by Taiyo Kagaku, Ltd., Japan, Decarf type) and a pH controller (Hirama Rikagaku Kenkyusho, Ltd., Japan, pH-CON-2 type).

After completion of the addition of phosphorus oxychloride, the mixture was stirred at the same temperature for additional 30 minutes. Pyridine was distilled off at 40° C. or below under reduced pressure. To the residue was added a 35% aqueous solution of hydrochloric acid to adjust the pH to 0.5. The amount of 2-phosphated ester of ascorbic acid in this solution and the yield percentage were determined according to the same manner as that described in Example 1.

For the analysis, to the reaction mixture was added water to bring the total volume to 1000 ml and 1 ml thereof was taken as a sample. As a result, the amount of 2-phosphated ester of ascorbic acid produced and the yield percentage thereof based on the VC used were 46.5 g and 83.1%, respectively.

EXAMPLES 4 to 6

According to the same manner as that described in Example 2, the reaction was conducted except that different phosphorylating agents were used.

The results of the analysis are shown in Table 1.

TABLE 1

| Ex. No. | Phosphorylating Agent | Amount (g) | Yield (%) |
|---|---|---|---|
| 4 | Tetrachloropyro-phosphoric acid | 23.4 | 81.0 |
| 5 | Dichlorophosphoric acid | 25.0 | 80.7 |
| 6 | Phosphorus oxychloride monohydrate | 25.0 | 81.5 |

COMPARATIVE EXAMPLE 1

The following reaction was conducted under a nitrogen atmosphere.

VC (10.0 g) was dissolved in a mixture of pyridine (25 ml) and water (100 ml) and the solution was cooled to 0 to 5° C. To the solution was added a 60 w/v% aqueous solution of potassium hydroxide (about 11 ml) to adjust the pH to 13.0. To the mixture was added dropwise phosphorus oxychloride (12.2 g) over 1.5 hours with maintaining the temperature of the reaction system at 0° to 10° C. and maintaining the pH of the reaction system at 13.0±0.1 by addition of a 60 w/v% aqueous solution of potassium hydroxide with a constant delivery pump (manufactured by Iwaki, Ltd., Japan, MM-2DS type) and a pH controller (Hirama Rikagaku Kenkyusho, Ltd., Japan, pH-CON-2 type). Then, the mixture was stirred at the same temperature for about 30 minutes. Pyridine was then distilled off at 40° C. or below under reduced pressure. To the residue was added a 35% aqueous solution of hydrochloric acid to adjust the pH to 0.5. The amount and the yield percentage of the 2-phosphated ester of ascorbic acid in this solution were determined according to the same manner as described in Example 1.

As a result, the amount of the 2-phosphated ester of ascorbic acid and the yield percentage thereof based on the VC used were 9.8 g and 67.4%, respectively.

COMPARATIVE EXAMPLE 2

According to the same manner as that described in Comparative Example 1, the reaction was conducted except that phosphorus oxychloride (13.9 g) was used. As a result, the amount of the 2-phosphated ester of ascorbic acid and the yield percentage thereof based on the VC used were 8.9 g and 61.2%, respectively.

EXAMPLE 7

The following reaction was conducted under a nitrogen atmosphere.

5,6-O-isopropylidene ascorbic acid (hereinafter abbreviated as IPVC) (10.0 g) was dissolved in a mixture of pyridine (7.4 ml) and water (193 ml), and the solution was cooled to 0° to 5° C. The pH of the solution was adjusted to 12.7 by the addition of a 60 w/v% aqueous solution of potassium hydroxide (about 9 ml). To the resulting mixture was added dropwise tetrachloropyrophosphoric acid (11.7 g) over about 1.5 hours with maintaining the reaction system at 0° to 10° C. and maintaining the pH thereof at 12.7±0.1 by adding a 60 w/v% aqueous solution of potassium hydroxide with a constant delivery pump (manufactured by Iwaki, Ltd., Japan, MM-2DS type) and a pH controller (Hirama Rikagaku Kenkyusho Ltd., Japan, pH-CON-2 type). Then, the resulting mixture was stirred at the same temperature for about 30 minutes. Pyridine was distilled off at 40° C or below under reduced pressure. To the residue was added a 35% aqueous solution of hydrochloric acid to adjust the pH to 0.5. The amount of 2-phosphated ester of ascorbic acid produced in this solution as well as the yield percentage thereof were analyzed under the HPLC conditions as described above. As an authentic sample, magnesium salt of 2-phosphated ester of ascorbic acid having a known purity was used. As a result, the amount of the 2-phosphated ester of ascorbic acid and the yield percentage based on the IPVC used were 10.8 g and 91.2%, respectively.

EXAMPLE 8

The following reaction was conducted under a nitrogen atmosphere.

IPVC (10.0 g) was dissolved in a mixture of pyridine (15 ml) and water (185 ml), and the solution was cooled to 0° to 5°. The pH thereof was adjusted to 12.7 by the addition of a 60 w/v% aqueous solution of potassium hydroxide (about 9 ml). To the mixture was added dropwise tetrachloropyrophosphoric acid (11.7 g) over about 1.5 hours with maintaining the temperature of the reaction system at 0 to 10° C. and maintaining the pH at 12.7±0.1 by the addition of a 60 w/v% aqueous solution of potassium hydroxide by using the same devices as those described in Example 2. The mixture was stirred at the same temperature for about 30 minutes. To the resulting mixture was added IPVC (10.0 g) over about 15 minutes with maintaining the pH at 12.7±0.1. To the resulting mixture was again added tetrachloropyrophosphoric acid (11.7 g) at 0° to 10° C. over about 1.5 hours with maintaining the pH at 12.7±0.1 by the addition of a 60 w/v% aqueous solution of potassium hydroxide, followed by stirring at the same temperature for additional 30 minutes. Pyridine was distilled off at 40° C. or below under reduced pressure. To the residue was added a 35% aqueous solution of hydrochloric acid to adjust the pH to 0.5. The amount of 2-phosphated ester of ascorbic acid in this solution and the yield percentage thereof were determined according to the same manner as that described in Example 7. As a result, the amount of 2-phosphated ester of ascorbic acid and the yield percentage thereof based on the IPVC used were 21.8 g and 92.0%, respectively.

EXAMPLE 9

The following reaction was conducted under a nitrogen atmosphere.

IPVC (47.5 g) was dissolved in a mixture of pyridine (15 ml) and water (50 ml). A 12 ml portion of the solution was added dropwise over 15 minutes to a mixture of pyridine (40 ml) and water (460 ml) cooled to 0° to 5° C. with maintaining the pH of the system at 12.8±0.1 by the addition of a 60 w/v% aqueous solution of potassium hydroxide with a constant delivery pump (manufactured by Taiyo Kagaku Kogyo, Ltd., Japan, Decarf type) and a pH controller (Hirama Rikagaku Kenkyusho, Ltd., Japan, pH-CON-2 type), and with cooling at 0° to 10° C.

Tetrachloropyrophosphoric acid (55.3 g) and the remaining IPVC solution were added dropwise simultaneously by using respective constant delivery pumps (Iwaki, Ltd., MM-2DS type) so that the addition of tetrachloropyrophosphoric acid was completed in 3 hours and that of the IPVC solution was completed in 2.5 hours with maintaining the pH of the system at 12.8±0.1 by the addition of a 60 w/v% aqueous solution of potassium hydroxide with a constant delivery pump (manufactured by Taiyo Kagaku Kogyo, Ltd., Japan, Decarf type) and a pH controller (Hirama Rikagaku Kenkyusho, Ltd., Japan, pH-CON-2 type), and with cooling at 0° to 10° C.

After completion of the addition of tetrachloropyrophosphoric acid, the mixture was stirred at the same temperature for additional 30 minutes. Pyridine was distilled off at 40° C. or below under reduced pressure. To the residue was added a 35% aqueous solution of hydrochloric acid to adjust the pH of the system to 0.5. The amount of 2-phosphated ester of ascorbic acid in this solution and the yield percentage thereof were determined according to the same manner as that described in Example 7.

For the analysis, water was added to the reaction mixture to bring the total volume to 1000 ml and 1 ml thereof was taken as a sample. As a result, the amount of 2-phosphated ester of ascorbic acid and the yield percentage thereof based on the IPVC used were 52.0 g and 92.4%, respectively.

EXAMPLES 10 and 12

According to the same manner as that described in Example 8, the reaction was conducted except that different phosphorylating agents were used. The results of analysis are shown in Table 2.

TABLE 2

| Ex. No. | Phosphorylating Agent | Amount (g) | Yield (%) |
|---|---|---|---|
| 10 | Phosphorous oxychloride | 28.6 | 91.0 |
| 11 | Dichlorophosphoric acid | 25.0 | 92.5 |
| 12 | Phosphorus oxychloride monohydrate | 25.0 | 91.8 |

COMPARATIVE EXAMPLE 3

The following reaction was conducted under a nitrogen atmosphere.

IPVC (12.30 g) was dissolved in a mixture of pyridine (25 ml) and water (100 ml). The solution was cooled to 0° to 5° C. and a 60 w/v% aqueous solution of potassium hydroxide (about 11 ml) to adjust the pH to 13.0. To the resulting solution was added dropwise phosphorus oxychloride (12.2 g) over 1.5 hours with maintaining the temperature of the system at 0° to 10° C. and maintaining the pH of the system at 13.0±0.1 by the addition of a 60 w/v% aqueous solution of potassium hydroxide with a constant delivery pump (manufactured by Iwaki, Ltd., Japan, MM-2DS type) and a pH controller (Hirama Rikagaku Kenkyusho, Ltd., Japan, pH-CON-2 type). The resulting mixture was stirred at the same temperature for about 30 minutes. After completion of the reaction, pyridine was distilled off at 40° C. or below under reduced pressure. To the residue was added a 35% aqueous solution of hydrochloric acid to adjust the pH to 0.5. The amount of 2-phosphated ester of ascorbic acid in this solution and the yield percentage thereof were determined by according to the same manner as that described in Example 7.

As a result, the amount of 2-phosphated ester of ascorbic acid and the yield percentage thereof based on the IPVC used were 11.1 g and 76.2%, respectively.

EXAMPLE 13

The following reaction was conducted under a nitrogen atmosphere.

Pyridine (40 ml) was added to water (460 ml) and the mixture was cooled to 0° to 5° C. To the mixture was added a 60 w/v% aqueous solution of potassium hydroxide (about 2 ml) to adjust the pH to 12.8. To this solution were added dropwise phosphorus oxychloride (67.4 g) and a VC solution [prepared by dissolving VC (38.5 g) in a mixture of pyridine (10 ml) and water (90 ml)]simultaneously at constant rates by using respective constant delivery pumps (Iwaki, Ltd., Japan, MM-2DS type) so that the addition of phosphorus oxychloride was completed in 3 hours and that of the VC solution was completed in 2.5 hours with maintaining the pH of the system at 12.8±0.1 by the addition of a 60 w/v% aqueous solution of potassium hydroxide (275 ml) with a constant delivery pump (manufactured by Taiyo Kagaku Kogyo, Ltd., Japan, Decarf type) and a pH controller (Hirama Rikagaku Kenkyusho, Ltd., Japan, pH-CON-2 type), and with cooling at 0° to 10° C.

After completion of the addition of phosphorus oxychloride, the mixture was stirred at the same temperature for additional 30 minutes. According to the same manner as that described in Example 3, the amount of 2-phosphated ester of ascorbic acid in this solution and the yield percentage thereof were determined. As a result, the amount of 2-phosphated ester of ascorbic acid and the yield percentage were 47.2 g and 84.2%, respectively.

TABLE 3

| Ex. No. | Phosphorylating Agent | Amount (g) | Yield (%) |
|---|---|---|---|
| 14 | Tetrachloropyrophosphoric acid | 55.5 | 84.1 |
| 15 | Dichlorophosphoric acid | 59.3 | 84.4 |
| 16 | Phosphorus oxychloride monohydrate | 59.3 | 84.5 |

EXAMPLES 14 and 16

According to the same manner as that described in Example 13, the reaction was conducted except that different phosphorylating agents were used.

The results are shown in Table 3.

EXAMPLE 17

The following reaction was conducted under a nitrogen atmosphere.

Pyridine (40 ml) was added to water (460 ml) and the mixture was cooled to 0° to 5° C. To the mixture was added a 60 w/v% aqueous solution of potassium hydroxide (about 2 ml) to adjust the pH to 12.8. To this solution were added dropwise tetrachloropyrophosphoric acid (55.3 g) and an IPVC solution [prepared by dissolving IPVC (47.5 g) in a mixture of pyridine (10 ml) and water (50 ml)]simultaneously at constant rates by using respective constant delivery pumps (Iwaki, Ltd., Japan, MM-2DS type) so that the addition of tetrachloropyrophosphoric acid was completed in 3 hours and that of the IPVC solution was completed in 2.5 hours with maintaining the pH of the system at 12.8±0.1 by the addition of a 60 w/v% aqueous solution of potassium hydroxide (275 ml) with a constant delivery pump (manufactured by Taiyo Kagaku Kogyo, Ltd., Japan, Decarf type) and a pH controller (Hirama Rikagaku Kenkyusho, Ltd., Japan, pH-CON-2 type), and with cooling at 0° to 10° C.

After completion of the addition of tetrachloropyrophosphoric acid, the mixture was stirred at the same temperature for additional 30 minutes. According to the same manner as that described in Example 3, the amount of 2-phosphated ester of ascorbic acid in this solution and the yield percentage thereof were determined. As a result, the amount of 2-phosphated ester of ascorbic acid and the yield percentage were 52.8 g and 93.9%, respectively.

EXAMPLES 18 to 20

According to the same manner as that described in Example 17, the reaction was conducted except that different phosphorylating agents were used.

The results are shown in Table 4.

TABLE 4

| Ex. No. | Phosphorylating Agent | Amount (g) | Yield (%) |
|---|---|---|---|
| 18 | Phosphorus oxychloride | 67.4 | 93.8 |
| 19 | Dichlorophosphoric acid | 59.3 | 93.5 |
| 20 | Phosphorus oxychloride monohydrate | 59.3 | 94.0 |

REFERENCE EXAMPLE

The solution obtained in Example 3 (pH 0.5) (999 ml) was passed through a column packed with activated charcoal (Shirasagi, special grade for chromatography manufactured by Takeda Chemical Industries, Ltd., Japan) (35 g) and soaked with water at SV 1, followed by passing a 3% aqueous solution of hydrochloric acid (1.8 liters). Then, a mixture (3470 ml) of phosphoric acid (93 g), 25% aqueous ammonia (122 g) and water (3300 g) (about pH 8) was passed through the column to collect an eluate (1.6 liters) containing 2-phosphated ester of ascorbic acid. The eluate was further passed through a column packed with a strong acidic ion-exchange resin (Diaion SK-110) (520 ml) to remove ammonia. To the eluate was added magnesium oxide (55 g) to convert the 2-phosphated ester of ascorbic acid into its magnesium salt and, at the same time, excess phosphoric acid was precipitated as magnesium phosphate. The precipitate was filtered off and the filtrate was passed through a column packed with activated charcoal (Shirasagi, special grade for chromatographic) (25 g), followed by elution with water (350 ml) to conduct decoloring. The decolorized solution was concentrated at temperature of not higher than 40° C. under reduced pressure to bring the volume to 450 ml. The concentrate was again decolorized with powdery activated charcoal (Shirasagi A, manufactured by Takeda Chemical Industries, Ltd., Japan) (3 g) and 90 v/v% methanol was added dropwise thereto to crystallize the magnesium salt. The crystals were collected by filtration and dried to obtain white magnesium salt of 2-phosphated ester of ascorbic acid (65.5 g).

This magnesium salt of 2-phosphated ester of ascorbic acid was analyzed by means of HPLC. As a result, the content of the product in terms of 2-phosphated ester of ascorbic acid was 60.7%, moisture content (determined by Karl Fischer's method) was 29.8%, and the content of magnesium was 8.9%. The yield calculated from the reaction mixture was 86.1%. The purity of the 2-phosphated ester of ascorbic acid determined by HPLC area percentage was 99.8%.

What is claimed is:

1. In an improved process for the production of 2-phosphated esters of ascorbic acid which comprises subjecting an ascorbic acid optionally protected at the 5- and 6-positions to phosphorylation, followed, if necessary, by removing any protecting group, the improvement is characterized by maintaining the concentration of the optionally protected ascorbic acid in a reaction mixture at less that 0.25M.

2. A process according to claim 1, wherein a mixture of ascorbic acid optionally protected at the 5- and 6-positions and a phosphorylating agent selected from the group consisting of phosphorus oxychloride, hydrates and alcoholate thereof, dichlorophosphoric acid and tetrachloropyrophosphoric acid is intermittently or continuously added dropwise to a reaction mixture to conduct phosphorylation.

3. A process according to claim 1, wherein phosphorylation is conducted in an atmosphere of nitrogen gas or argon gas.

4. A process according to claim 1, wherein phosphorylation is conducted in the presence of pyridine.

5. A process according to claim 1, wherein the optionally protected ascorbic acid is a compound selected from the group consisting of ascorbic acid, 5,6-O-isopropylidene ascorbic acid, 5,6-O-sec-butylidene ascorbic acid, 5,6-O-1-ethylbutylidene ascorbic acid, 5,6-O-cyclopentylidene ascorbic acid and 5,6-O-cyclohexylidene ascorbic acid.

6. A process according to claim 1, wherein the optionally protected ascorbic acid is ascorbic acid or 5,6-O-isopropylidene ascorbic acid.

7. A process according to claim 1, wherein the concentration of the optionally protected ascorbic acid in the reaction mixture is 0.25M or lower.

8. A process according to claim 1, wherein phosphorylation is conducted by using a phosphorylating agent in an amount of about 1.5 to about 2.5 times equivalent based on the optionally protected ascorbic acid used.

9. A process according to claim 1, wherein phosphorylation is conducted at pH 12.5 to 13.5.

10. A process according to claim 1, wherein the deprotection is conducted by adjusting the pH of the reaction mixture to pH 1 or lower.

11. In an improved process for the production of 2-phosphated esters of ascorbic acid which comprises subjecting an ascorbic acid optionally protected at the 5- and 6-positions to phosphorylation, followed, if necessary, by removing any protective group, the improvement is characterized by maintaining the concentration of the optionally protected ascorbic acid in a reaction mixture at less than 0.25M, said optionally protected ascorbic acid being a compound selected from the group consisting of ascorbic acid, 5,6-O-isopropylidene ascorbic acid, 5,6-O-sec-butylidene ascorbic acid, 5,6-O-1-ethylbutylidene ascorbic acid, 5,6O-cyclopentylidene ascorbic acid and 5,6-O-cyclohexylidene ascorbic acid, and said phosphorylation being conducted by intermittently or continuously adding dropwise a mixture of said optionally protected ascorbic acid and a phosphorylating agent selected from the group consisting of phosphorus oxychloride, hydrates and alcoholates thereof, dichlorophosphoric acid and tetrachloropyrophosphoric acid to the reaction mixture in the presence of pyridine in an atmosphere of nitrogen gas or argon gas.

* * * * *